(12) United States Patent
Legrand

(10) Patent No.: US 6,524,852 B1
(45) Date of Patent: Feb. 25, 2003

(54) REMOVING OR INCREASING PERMEABILITY OF EMBRYONIC CAPSULE TO PREPARE EQUINE EMBRYOS FOR CRYOPRESERVATION

(75) Inventor: Emmanuel Legrand, Les Rouges Verts, 61200 Sevigny (FR)

(73) Assignees: Emmanuel Legrand, Sevigny (FR); Rene Legrand, Sevigny (FR); Odile Legrand, Sevigny (FR); Richard Legrand, Sevigny (FR); Jean-Pierre Legrand, Sevigny (FR); Corinne Legrand Buisson, Bailleul (FR)

( * ) Notice: Subject to any disclaimer, the term of this patent is extended or adjusted under 35 U.S.C. 154(b) by 0 days.

(21) Appl. No.: 09/445,740

(22) PCT Filed: Jun. 10, 1998

(86) PCT No.: PCT/FR98/01190

§ 371 (c)(1),
(2), (4) Date: Feb. 1, 2000

(87) PCT Pub. No.: WO98/56246

PCT Pub. Date: Dec. 17, 1998

(30) Foreign Application Priority Data

Jun. 10, 1997 (FR) ............................................. 97 07311

(51) Int. Cl.⁷ ............................. A01N 1/00; A01N 1/02; A01N 63/00; C12N 5/00; C12N 5/02
(52) U.S. Cl. ........................ 435/325; 435/1.3; 424/93.7
(58) Field of Search ................................. 435/325, 404, 435/213, 817, 1.3; 424/93.7

(56) References Cited

U.S. PATENT DOCUMENTS 4,530,816 A * 7/1985 Douglas-Hamilton .......... 422/1
5,817,453 A * 10/1998 Brinster ....................... 435/1.1
6,037,175 A * 3/2000 Cameron et al. ............ 435/374

OTHER PUBLICATIONS

S–I Hochi et al., "Influence of Relative Embryonic Volumes During Glycerol Equilibration on the Survival of Frozen–Thawed Equine Blastocysts", *Journal of Reproduction and Development*, vol. 40, No. 3, 1994, pp. 243–249.

K Hinrichs, Embryo Transfer in the Mare: A Status Report, *Animal Reproduction Science*, vol. 33 (1–4), 1993, pp 227–240.

J. G. Oriol et al., "Mucin–Like Glycoproteins in the Equine Embryonic Capsule", *Mol Reprod Dev*, vol. 34, No. 3, 1993, pp. 255–265.

K. E. Hehnke et al., "Formation and Characterization of Vesicles Form Day–10 Horse Conceptuses", *Theriogenology*, vol. 34, No. 4, 1990, pp 709–720.

Y. Yamamoto et al., "Frozen Storage of Equine Embryos", *J Fac Agric Hokkaido Univ*, vol. 62, No. 2, 1985, pp. 182–210.

* cited by examiner

Primary Examiner—David M. Naff
Assistant Examiner—Deborah K. Ware
(74) Attorney, Agent, or Firm—Young & Thompson

(57) ABSTRACT

A method for preparing an equine embryo for cryopreservation is provided. The method includes collecting an equine embryo with its embryonic capsule. Then after collection the embryo is treated to eliminate or increase the permeability of the capsule in which to enhance subsequent action of cryoprotectant(s). After the treatment the embryo is contacted with cryoprotectant(s) and then placed in a straw with the cryoprotectant(s). Furthermore, the capsule can be treated with enzymes such as collagenase and/or trypsin. Also the embryonic capsule may be removed by mechanical means before subjecting it to the action of cryoprotectant(s). The embryo may also be subjected to an enzymatic treatment to weaken the capsule.

10 Claims, No Drawings

REMOVING OR INCREASING PERMEABILITY OF EMBRYONIC CAPSULE TO PREPARE EQUINE EMBRYOS FOR CRYOPRESERVATION

BRIEF DESCRIPTION OF THE INVENTION

1. Field of the Invention

This invention relates to the field of the preservation of embryos at low temperatures; it more particularly relates to an improvement in the methods of preparation of equine embryos for cryopreservation (freezing or vitrification), especially for subsequent transplantation.

The freezing of embryos during embryo transfers has many advantages. Amongst others, it removes the need to synchronize the oestral cycles of the donor and the recipient; it simplifies the transport of embryos over long distances and it also makes the creation of embryo banks possible, especially for rare animals or endangered species.

2. Description of the Related Art

After the first successes in the 1970's, embryo freezing has now become a routine technique in domestic ruminants, especially cattle.

Parallel work carried out in the equine field led to the first births of foals from frozen embryos at the beginning of the 1980's.

Biologically, the fecundation of the equine embryo takes place in the oviduct, at the junction between the ampulla and the isthmus, generally 12 hours after ovulation. The embryo then develops in the oviduct; it passes from the unicellular zygotic stage, from 100 to 160 $\mu$m in size, to the morula stage at from 16 to 32 cells (150 to 200 $\mu$m). The mitotic divisions at first take place simultaneously in the different blastomeres, then more and more asynchronously. The development phase of the equine embryo in the oviduct lasts about 5 days.

The blastocyte stage follows the morula stage at about the point when the embryo passes into the uterus. It is at this stage that differentiation between two cell populations takes place: the trophoblast and the inner cell mass which becomes the foetus.

At this stage, the embryo is composed of a liquid cavity (the blastocoel), surrounded by a cellular layer (the trophoblast), next to the inner cell mass. Around the embryo are two acellular structures, the pellucid zone and the capsule.

The pellucid zone is of the order of 15 to 30 $\mu$m thick; it is composed of a dense inner layer, with a small number of fine canals, and an outer layer containing large lacunae. This pellucid zone is present in the ovocyte and disappears around the 7th or 8th day.

The capsule is specific to equine embryos. It is formed in about 8 hours after the embryo enters the uterus, between the trophoblast and the pellucid zone. This capsule is composed of glycoproteins. Its thickness increases steadily up to a peak at about the 18th day, and then decreases until it disappears at around the 22nd day, at about the time when the embryo is fixed in the uterus.

Embryos intended for freezing must be collected before they are fixed in the uterus. The suitable time is evaluated, after covering or insemination, by transrectal palpation and from echotomographic data.

This collection may be made very soon after fecundation, in the oviduct, but this requires a surgical operation which is traumatic for the animal. The other solution is to wait until the embryo reaches the uterus (after the 6th day after fecundation) and to collect through the vagina, using a suitable collection probe, following the technique of LAGNEAUX D. et al. (1988, "la transplantation embryonnaire chez la jument", CEREOPA, $14^{th}$ day, 163–181). This probe can be used to introduce a collection medium into the uterus (for example Dubelco's phosphate buffered saline (PBS)+2 g/l of bovine serum albumin, available from I.M.V. (Instrument de Médecine Vétérinaire), B.P. 81, 61 L'AIGLE (France)), then to recover it with the possible embryo(s). The recovery medium is examined with a binocular microscope and, if embryos are found, they are isolated in a small vessel containing the same medium (PBS+albumin).

The embryo is then prepared to support the subsequent freezing operation. This preparation consists of subjecting it to the action of cryoprotectants whose particular function is to prevent the formation of intracellular crystals during the reduction in temperature. The cryoprotectants used may be selected from glycerol, dimethyl sulfoxide (DMSO), ethylene glycol, or 1,2-propanediol ; they are used in concentrations of the order of 1 to 2M, for a duration of 10 to 30 min (these concentrations and times are varied according to the protection efficiency desired, taking account of the possible toxicity of the products). The embryo is preferably subjected to successive baths of cryoprotectants in increasing concentration.

The embryo is then placed in a plastic straw with a small amount of the medium corresponding to the final bath of cryoprotectant, and this straw is then placed in the freezing compartment of a programmable freezer at a temperature of about –7° C. After an equilibration time of about 5 to 10 min, the crystallization of the contents is induced by contact with a metal rod previously cooled in liquid nitrogen (–196° C.). After a further time for thermal equilibrium, the freezer programmer reduces the temperature to about –30° C./–35° C., at a rate of –0.1 to 1° C. per minute; at this temperature, the straw is immersed in liquid nitrogen, then stored in a tank.

Thawing, before transfer, is achieved by immersing the straw in a water-bath at 37° C. for 1 min; the embryo is taken out and the operation of removing the cryoprotectant is performed by a succession of dilutions in baths of decreasing concentration.

The embryo is then ready for transfer into the recipient mare. Two techniques are used conventionally : the first, surgical, consists of implanting the embryo in the oviduct; the second, non-surgical and better corresponding to the objectives of commercial transfer, consists of placing the embryo in the uterus using a probe to pass through the cervix.

The technique described above is derived from that used for many years in cattle, and which in cattle gives a gestation rate of greater than 50% from frozen embryos.

However, in the equine field, the gestation rates obtained are very low, only of the order of 20 to 30%.

It has only recently been found that the use of this freezing technique in equines led to significant necroses in the inner cell mass and trophoblast of the embryo, and this seemed to be the cause of the high number of premature abortions.

SUMMARY OF THE INVENTION

The aim of the present invention is to provide an improved technique for preparing the embryos for cryopreservation, which leads to a reduced level of the necroses associated with this operation, and in consequence favourizes the subsequent gestation after the embryo transfer.

The method according to the present invention is based on the presence of the capsule which surrounds the embryo for the greater part of the time which the embryo spends in the uterus of the donor, and on the hypothesis that the presence of this capsule hinders the operations of preparing the embryo before freezing.

In order to achieve an acceptable collection level, the embryos are collected fairly late; as a general rule, they are at the blastocyte stage and surrounded by a capsule.

In the conventional sequence of operations for preparing equine embryos for cryopreservation, the method according to the invention consists of, prior to subjecting said embryo to the action of cryoprotectants, subjecting it to an appropriate treatment to eliminate the embryonic capsule or to increase the permeability of this capsule, in order to reinforce the subsequent action of said cryoprotectant(s).

DETAILED DESCRIPTION OF THE PREFERRED EMBODIMENTS

According to a first embodiment, the capsule is destroyed or simply made more permeable by an appropriate chemical or enzymatic technique, for example based on collagenase or trypsin. The concentrations of the products used and the contact times (bath treatments) are selected so that the capsule is at least partially lysed while taking account of the possible toxicity of the products so as not to harm the embryo. Since the sites of action of trypsin and collagenase are different, the use of a mixture of these two enzymes may be envisaged.

According to another technique, the capsule is treated mechanically: it is partially or completely removed, or simply pierced. This mechanical treatment is advantageously preceded by a suitable chemical or enzymatic technique to weaken said capsule.

EXAMPLE 1

The embryo is collected 5 to 8 days after ovulation. After isolation, it is placed in an intermediate bath (PBS medium+2 g/l of bovine serum albumin ultrafiltered over a 0.2 $\mu$m filter to avoid bacterial contamination).

The embryo is then placed in a 2 ml vessel containing 1 to 2 ml of a solution of trypsin at 0.2% concentration (dilution in a PBS medium without calcium or magnesium) for 15 minutes at ambient temperature (about 23° C.).

A greater or lesser degree of destruction or weakening of the capsule is obtained as a function of its original size. A thinner residual capsule may remain around the embryo; this residual capsule may be completely destroyed by simple enzymatic action, or said enzymatic action may be complemented by a mechanical decapsulation performed using a micromanipulation technique.

To dilute the enzyme and stop its action, the embryo is placed in three or four successive baths of ultrafiltered PBS medium+albumin, for a total time of 10 min.

At the end of this 10 min period, the embryo is placed in the first bath of cryoprotectant (0.5M glycerol for 15 min), then in the second bath (1M glycerol for 15 min), and finally in the third bath (1.5M glycerol for 15 min).

The embryo is then placed in the straw, and subjected to the normal operations to freeze it, as described above.

Thawing is performed by immersing the straw in a water bath at 37° C. for 1 min, and the operations to remove the cryoprotectant are then performed: the embryo is placed in a first bath of 1M glycerol+0.25M sucrose for 15 min, then in a second bath of 0.5M glycerol+0.25M sucrose for 15 min, then in a third bath (0.25M sucrose for 15 min) and finally in PBS medium+albumin (15 minutes).

The embryo is then ready for transfer.

EXAMPLE 2

The protocol of the previous example is repeated except that the 0.2% trypsin is replaced by type II collagenase at a concentration of 2.5% for 15 min (also diluted in PBS medium without calcium or magnesium).

Results a) Cell Necrosis

Cell necrosis denotes the structural modifications which follow the death of a cell; it results from the progressive degradation of the cell by its own enzymes contained in the lysosomes.

The percentage of necrotic cells is representative of the cell damage caused by the manipulations and reflects the viability of the embryo.

This histological examination is carried out according to the technique described by J. F. BRUYAS—1994—"Contribution á l'étude de la congelation des embryos équins: une approche métabolique et cellulaire"—Research dissertation in pathology and reproduction—Ecole Nationale Veterinaire de Nantes, France. It is performed before the freezing operation to determine the cell damage associated with the preparation treatment.

The percentage of necrotic cells observed was the following:

a) embryos treated with trypsin (according to example 1): 11% (1 embryo analysed)

b) embryos treated with collagenase (according to example 2): 10.3% (one embryo analysed).

These results may be compared with the necrosis rate of embryos having followed the same preparation protocol, without the enzymatic treatment c) embryos without capsule: 13.9% (mean of 6 embryos)

d) embryos with capsule: 30.6% (mean of 8 embryos).

It can thus be seen that the embryos whose capsule has been treated with an enzyme undergo less damage than the embryos which have retained an intact capsule.

These treated embryos behave like the embryos without capsule.

b) In Vivo Tests 8 embryos were collected between the 5th and 8th day after ovulation according to the method of LAGNEAUX et al. described above.

The age distribution of the embryos collected was the following:

| Age of embryos | Number of embryos |
| --- | --- |
| 5.5 days | 1 |
| 6.5 days | 1 |
| 7.5 days | 2 |
| 8.5 days | 4 |

The sizes of the embryos collected were the following:

| Embryo N° | Size (μm) | Embryo N° | Size (μm) |
| --- | --- | --- | --- |
| 1 | 1020 | 5 | 187 |
| 2 | 714 | 6 | 1581 |
| 3 | 119 | 7 | 1105 |
| 4 | 442 | 8 | 187 |

These embryos were treated as in example 1 above.

Embryos n° 1 and n° 2 were subjected to mechanical decapsulation after the enzymic treatment and the capsules of embryos n° 6 and n° 7 were completely lysed in the enzyme bath.

This thus gave two batches of embryos:

batch n° 1 with embryos without capsule (embryos n° 1, n° 2, n° 6 and n° 7), and batch n° 2 with embryos with an only partially lysed capsule (embryos n° 3, n°4, n° 5 and n° 8).

After thawing, the transfer technique used was that reported by TAIMTURIER D., BRUYAS J. F., DUMONT P., FIENI F., ESCOUFLAIRE P. (1989, "La transportation embryonnaire chez la jument", Revue Med. Vet. 140, 1109–1115), which consists of placing the embryo behind the cervix using a transplantation syringe.

Gestation was monitored by an echotomographic technique (scanner 100 from Pie Medical, Hospimedi 60790 POUILLY, FRANCE), at 14, 21 and 28 days.

The results of the transfers are given in the table below:

| Batch | Embryo n° | GD 14 | GD 21 | GD 28 |
| --- | --- | --- | --- | --- |
| 1 | 1 | + | − | − |
| 1 | 2 | − | − | − |
| 2 | 3 | − | − | − |
| 2 | 4 | + | (a) | (a) |
| 2 | 5 | + | − | − |
| 1 | 6 | + | + | + |
| 1 | 7 | + | + | + |
| 2 | 8 | + | + | + |

GD = Gestation diagnosis (at 14, 21 and 28 days respectively)
(a): the recipient mare was injured after the gestation diagnosis at 14 days.

The examinations were therefore discontinued.

The gestation rates at 14, 21 and 28 days were as follows:

| Gestation diagnosis | Number of gestations/ Number of transfers | % |
| --- | --- | --- |
| at 14 days | 6/8 | 75% |
| at 21 days | 3/7 | 43% |
| at 28 days | 3/7 | 43% |

These rates are overall higher than those obtained with previously known protocols; they are similar to the rates obtained after transfer of fresh embryos (58% on average over the last 10 years (CLEMENT F., HOFFERER S. VINCENT P., 1995 "La transplantation embryonnaire chez la jument", Equ'idée March–April 17, 56–62).

Batch n° 1 (embryos without capsule)

| Gestation diagnosis | Number of gestations/ Number of transfers | % |
| --- | --- | --- |
| at 14 days | 3/4 | 75% |
| at 21 days | 2/4 | 50% |
| at 28 days | 2/4 | 50% |

Batch n° 2 (embryos with partially lysed capsule)

| Gestation diagnosis | Number of gestations/ Number of transfers | % |
| --- | --- | --- |
| at 14 days | 3/4 | 75% |
| at 21 days | 1/3 | 33% |
| at 28 days | 1/3 | 33% |

These results show that it is possible to achieve gestations with embryos which no longer have their capsule, and that there is no significant difference between the results from embryos transplanted without capsule and embryos transplanted with a capsule.

The gestation rates as a function of age were:

| Age | D14 | D21 | D28 |
| --- | --- | --- | --- |
| 5.5 days | 0/1 | 0/1 | 0/1 |
| 6.5 days | 1/1 | 1/1 | 1/1 |
| 7.5 days | 2/2 | 0/1 | 0/1 |
| 8.5 days | 3/4 | 2/4 | 2/4 |

These results show that it is possible to achieve gestation from frozen embryos aged 7.5 days or more, by using the method according to the invention, while this had not in practice been achieved until now by known methods.

The gestation rates as a function of size were as follows:

| Size | D14 | D21 | D28 |
| --- | --- | --- | --- |
| <200 μm | 2/3 | 1/3 | 1/3 |
| between 200 and 500 μm | 1/1 | 0/0 | 0/0 |

-continued

| Size | D14 | D21 | D28 |
| --- | --- | --- | --- |
| >500 µm | 3/4 | 2/4 | 2/4 |
| >1000 µm | 3/3 | 2/3 | 2/3 |

These results show that it is possible to achieve gestation from frozen embryos greater than 500 µm in size by using the method according to the invention, while this had not been achieved until now by known methods.

The results overall show the importance of the embryonic capsule in the cryopreservation process for equine embryos. The method according to the invention improves the gestation rates from frozen embryos and shows the possibilities of commercial development of this technology.

The treatment of the embryonic capsule reduces the importance of the time at which the embryo is collected. In particular, the collection may be performed fairly late: there is thus a high collection rate and the freezing operation is performed on embryos at the blastocyte stage, which makes them better able to withstand the stress of the different treatments.

What is claimed is:

1. Method for preparing an equine embryo for cryopreservation, said method comprising collecting an equine embryo having an embryonic capsule, subjecting the collected embryo to treatment to eliminate the embryonic capsule, or to increase permeability of the embryonic capsule to enhance subsequent action of cryoprotectant(s), contacting the treated embryo with cryoprotectant(s), and placing the treated embryo and cryoprotectant(s) in a straw to obtain said equine embryo for cryopreservation.

2. Method according to claim 1, wherein said treatment to eliminate, or increase permeability of the embryonic capsule is by enzymatic action.

3. Method according to claim 2, wherein said treatment is by immersing the embryo in a bath of collagenase.

4. Method according to claim 3, wherein said treatment is with 2.5% collagenase for 15 min at ambient temperature.

5. Method according to claim 2, wherein said treatment is by immersing the embryo in a bath of trypsin.

6. Method according to claim 5, wherein said treatment is with 0.2% trypsin for 15 min at ambient temperature.

7. Method according to claim 2, wherein said treatment is with a mixture of collagenase and trypsin.

8. Method according to claim 1, wherein said treatment to eliminate, or increase permeability of the embryonic capsule is performed mechanically.

9. Method according to claim 8, wherein before said treatment said embryo is subjected a to chemical treatment to weaken said capsule.

10. Method according to claim 9, wherein before said treatment, said embryo is subjected to an enzymatic treatment to weaken the capsule.

* * * * *